United States Patent [19]

Lee et al.

[11] 4,148,695
[45] Apr. 10, 1979

[54] PREPARATION AND RECOVERY OF ETHERS

[75] Inventors: Kung-You Lee; Richard V. Kessler; Uygur Kokturk, all of Wappingers Falls, N.Y.

[73] Assignee: Texaco Inc., New York, N.Y.

[21] Appl. No.: 928,500

[22] Filed: Jul. 27, 1978

[51] Int. Cl.² .................. B01D 3/40; C07C 41/12
[52] U.S. Cl. .................................. 203/63; 203/64; 568/697; 568/699
[58] Field of Search .......... 203/614 A, 616; 203/63, 203/64, 84, 38

[56] References Cited

U.S. PATENT DOCUMENTS

| | | | |
|---|---|---|---|
| 2,720,547 | 10/1955 | Wolff et al. | 203/63 |
| 2,721,222 | 10/1955 | Cottle et al. | 203/63 |
| 3,446,853 | 5/1969 | Newton et al. | 203/63 |
| 3,940,450 | 2/1976 | Lee | 203/70 |

Primary Examiner—Wilbur L. Bascomb, Jr.
Attorney, Agent, or Firm—Thomas H. Whaley; Carl G. Ries; Carl G. Seutter

[57] ABSTRACT

Methyl t-butyl ether may be recovered from etherification reaction effluent by extractive distillation in the presence of n-butanol.

11 Claims, 1 Drawing Figure

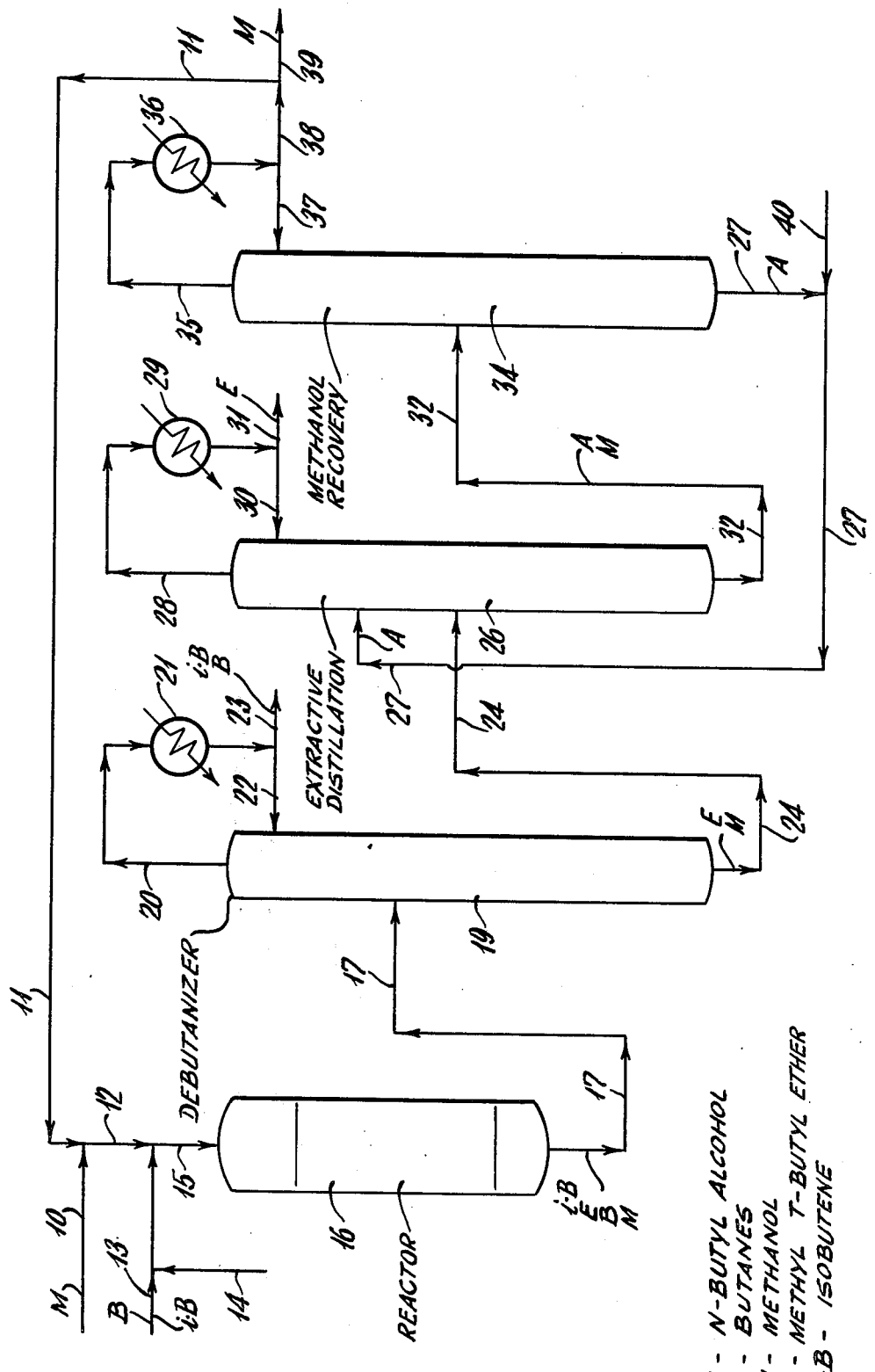

PREPARATION AND RECOVERY OF ETHERS

FIELD OF THE INVENTION

This invention relates to the preparation of ethers. More particularly it relates to the preparation of unsymmetrical ethers in high yield and purity.

BACKGROUND OF THE INVENTION

As is well known to those skiled in the art, ethers, including unsymmetrical ethers, may be prepared by reacting an alcohol with an olefin or with another alcohol to form the desired product. The reaction mixture, containing catalyst and/or condensing agent may be separated and further treated to permit attainment of desired product. Such further treatment commonly includes one or more distillation operations.

It is an object of this invention to provide a process for preparing ethers. Other objects will be apparent to those skilled in the art from the following description.

SUMMARY OF THE INVENTION

In accordance with certain of its aspects, the novel method of this invention for preparing a desired product ether may comprise distilling a reaction mixture containing (i) a lower alkanol and (ii) an ether of said lower alkanol and t-butyl alcohol or t-amyl alcohol in an extractive distillation operation in the presence of, as an extractive distillation medium, a $C_2$–$C_8$ aliphatic alcohol having a higher boiling point than said lower alkanol and being substantially miscible therewith thereby forming (i) extractive distillation overhead containing said ether and (ii) extractive distillation bottoms containing said lower alkanol and extractive distillation medium; recovering said extractive distillation overhead containing said ether; distilling said extractive distillation bottoms in a distillation operation thereby forming distillation operation overhead containing lower akanol and distillation operation bottoms containing said extractive distillation medium; recovering said distillation operation overhead containing lower alkanol; recovering said distillation operation bottoms containing said extractive distillation medium; and passing said distillation operation bottoms containing said extractive distillation medium to said extractive distillation operation.

DESCRIPTION OF THE INVENTION

The lower alkanol which may be used to form the desired product ethers which may be recovered by the process of this invention may contain 1–3 carbons—typified by methanol, ethanol, normal propanol, and iso-propanol. The advantages attained by the process of this invention are believed to be most significant when the lower alkanol is methanol or ethanol; and for purposes of disclosing the invention most clearly, reference is hereafter made to methanol as the lower alkanol. It will be apparent the ethanol etc. may be used where methanol is set forth.

The charge hydrocarbon which is reacted with the lower alkanol to form the product ether which may be recovered by the process of this invention is preferably isobutene or an isopentene contained in a hydrocarbon stream. For convenience of description, reference is hereafter made to isobutene.

The charge hydrocarbon may be recovered in a stream identified as a B-B stream which contains primarily $C_4$ hydrocarbons, predominantly butanes and i-butene.

The product ether which is to be recovered is typically one of the following:

methyl t-butyl ether
methyl t-amyl ether
ethyl t-butyl ether
ethyl t-amyl ether
etc.

It will be apparent that a mixture of ethers may be obtained by use of a mixture of eg methanol and ethanol as the charge alkanol or of a mixture of eg isobutene and isopentene as the charge olefin. For purpose of convenience of description, reference is hereafter made to methyl t-butyl ether as the desired product ether.

Preparation of the product ether which may be recovered by the process of this invention may be carried out typically by reacting methanol with isobutylene (i.e. isobutene). Although the reactants may be impure, it is preferred that they be of reasonable purity. Hydrocabon impurities, if present eg in the isobutene stream may readily be removed after etherification.

Reaction may be carried out utilizing the following reaction conditions:

TABLE

| Conditions | Broad Range | Preferred Range | Preferred Value |
|---|---|---|---|
| Temperature ° F. | 100–300 | 150–250 | 200 |
| Pressure psig | 50–750 | 50–500 | 300 |
| Methanol (parts) | 150–1500 | 150–600 | 500 |
| Isobutene (parts) | 150–1500 | 150–700 | 500 |

The charge isobutene may be present as a portion of a hydrocarbon stream which contains inerts such isobutane which do not react during the course of reaction; when this is the case they will be removed, as by distillation, from the product stream.

It is a particular feature of the process of this invention that the mole ratio of the methanol to the isobutene may be at least about 0.8. It will be found however that the advantages inherent in the process may be attained to a greater degree if this ratio is greater than 1 and preferably 1.2–4.0, say 2.0. Presence of the excess of e.g. methanol is to assure the high conversion of isobutene.

Etherification may be preferably carried out in the presence of a solid resin etherification catalyst. These catalysts are preferably relatively high molecular weight carbonaceous materials containing at least one —$SO_3H$ group as the functional group. Typical of these catalysts are the sulfonated coals ("Zeo-Karb H," "Nalcite X" and "Nalcite AX") produced by the treatment of bituminous coals with sulfuric acid. These materials are usually available in a neutralized form and in this case must be activated to the hydrogen form by treatment with a strong mineral acid such as hydrochloric acid, followed by water washing to remove sodium and chloride ions prior to use.

The sulfonated resin type catalysts are preferred for use in the present invention. These catalysts include the reaction products of phenol-formaldehyde resins and sulfuric acid ("Amberlite IR-1," "Amberlite IR-100," and "Nalcite MX"). Also useful are the sulfonated resinous polymers of coumarone-indene with cyclopentadiene, sulfonated polymers of coumarone-indene with furfural; sulfonated polymers of coumarone-indene with cyclopentadiene and furfural; and sulfonated polymers of cyclopentadiene with furfural.

The most preferred cationic exchange resins are strongly acidic exchange resins consisting essentially of sulfonated polystyrene resin, for instance, a divinylbenzene cross-linked polystyrene matrix having 0.5–20% and preferably 4–16% of copolymerized divinylbenzene therein, bearing ionizable or functional nuclear sulfonic acid groups. These resins are manufactured and sold commercially under various trade names such as "Dowex50," "Nalcite HCR," and "Amberlyst15". As commercially obtained they have a solvent content of about 50% and can be used as is or the solvent can be removed first. The resin particle size may typically be 10 to 50 mesh (U.S. Sieve Series)

The reaction may be carried out in either a stirred slurry reactor or in a fixed bed continuous flow reactor. The catalyst concentration should be sufficient to provide the desired catalytic effect. Generally in a stirred reactor, catalyst concentration should be 0.1–10% (dry basis) by weight of the reactor contents, 0.2 to 5% being the preferred range.

There may thus be added to the reaction operation in the preferred embodiment, 500 parts of the methanol and 500 parts of isobutene. During reaction, the desired product methyl terbutyl ether is formed by reaction of methanol and isobutene. Etherification is preferably carried out at 100° F.–300° F., preferably 150° F.–250° F., say 200° F.; and the pressure may be 50–750 psig, preferably 50–500 psig, say 300 psig. The typical crude product stream may contain 214–414 parts, say 273 parts of methanol, 0–350 parts, say 102 parts of isobutene, and 236–786 parts, say 625 parts of methyl tertiary butyl ether.

The crude product stream so obtained is passed to a debutanizer which is operated under pressure, say 100 psig. The typical crude product stream, at 150° F.–250° F., say 200°0 F. at 50–500 psig, say 300 psig, is passed to this debutanizing operation. (It will be apparent to those skilled in the art that if the reaction has been carried out to convert isopentene to the corresponding t-amyl ether, then this debutanizing operation may more properly be referred to as a de-pentanizing operation or still more generally as a hydrocarbon stripping operation). In the debutanizing operation, the overhead may contain unreacted isobutene (and/or isopentene) plus inerts such as butanes including n-butanes).

Overhead from the debutanizing operation at 100 psig, and 150° F.–170° F., say 160° F. is condensed at 110° F. and a portion may be returned as reflux. Net overhead typically contains 0–350 parts, say 102 parts of isobutene and 3670–4500 parts, say 4045 parts of unreacted hydrocarbons including alkanes such as butanes and pentanes. Depending on the content of inerts, the overhead may be (i) withdrawn from the system, (ii) purified of inerts and recycled to etherification, or (iii) recycled without purification.

Debutanizer bottoms recovered at 200° F.–240° F., say 220° F. and 100 psig contains 236–786 parts, say 625 parts of methyl t-butyl ether and 214–414 parts, say 273 parts of methanol. This stream, in total amount of 650–1000 parts, say 898 parts, is at 200° F.–240° F., say 220° F. at 100 psig and passed to the extractive distillation operation which is operated at 0 psig.

There is also admitted to the extractive distillation operation, at an upper portion of the distillation column, an extractive distillation medium.

The extractive distillation medium employed in practice of the process of this invention may be characterized by the following criteria:

1. It is a $C_2$ to $C_8$ (preferably a $C_4$ to $C_6$) aliphatic, preferably monohydroxy, alcohol;
2. It has a higher boiling point (preferably 50° F.–150° F., say 90° F. higher) than does the lower alkanol which is contained in the charge mixture;
3. It preferably contains at least two more carbon atoms than does the lower alkanol which is contained in the charge mixture,
4. It is at least partially miscible, and preferably substantially completely miscible, with the lower alkanol which is contained in the charge mixture; and
5. It forms a mixture with the lower alkanol to be separated from the desired product ether, which mixture has a vapor pressure (at the conditions of extractive distillation) which is lower than the vapor pressure of the desired product ether.

It will be apparent to those skilled in the art that although it is possible to utilize ethanol in the extractive distillation to separate methanol, clearly it is more preferred to utilize a $C_4$ to $C_8$ alcohol, preferably n-butanol in this separation. Subject to the criteria noted supra, the following alcohols may be employed:

Table

| |
|---|
| ethanol |
| n-propanol |
| i-propanol |
| n-butanol |
| i-butanol |
| s-butane |
| n-pentanol |
| i-pentanol |
| hexanols |
| heptanols |
| potanols etc. |
| glycerin |
| ethylene glycol |
| propylene glycol |
| tri methylol propane |

Commercial mixtures of alcohols may be employed including those identified as eg octanols (which may be principally 2-ethylhexanol), hexanols (which may include a wide variety of isomers), etc.

Preferred alcohols may include n-butanol; 2-ethylhexanols; amyl alcohols; and glycerin.

When the charge lower alkanol to be removed is methanol, the preferred extractive distillation medium may be normal or isobutanol, most preferably n-butanol. When the charge lower alkanol to be removed is ethanol, a preferred extractive distillation medium may be a $C_4$ or a $C_5$ alcohol, most preferably n-butanol.

For purposes of convenience, the extractive distillation medium will be hereafter referred to as n-butanol.

Extractive distillation medium eg n-butanol is preferably added to the extractive distillation column in amount of 2140–4140 parts, say 2730 parts at 180° F.–230° F., say 200° F. Preferably the extractive distillation medium, eg n-butanol is added in amount of 5–20 parts, say 10 parts, per part of methanol contained in the ether-methanol charge to the extractive distillation operation.

Extractive distillation overhead, recovered at 129° F.–133° F., say 131° F. and 0 psig, contains substantially pure methyl t-butyl ether in amount of 236–786 parts, say 625 parts. This overhead is condensed and recovered as net product—methyl t-butyl ether.

Bottoms from extractive distillation, recovered at 210° F.–250° F., say 220° F. contains 214–414 parts, say 273 parts of methaol and 2140–4140 parts, say 2730 parts of n-butanol. This stream is passed to methanol recovery operation at 0 psig. Overhead from this distillation operation, recovered at 147° F.–151° F., say 149° F. is condensed and a portion is returned as reflux. Net methanol product, in amount of 214–414 parts, say 273 parts, is recycled to the etherification operation.

Bottoms from the methanol recovery distillation tower, recovered at 240° F.–250° F., say 243° F. include 2140–4140 parts, say 2730 parts of extractive distillation medium, typically n-butanol. This distillation operation bottoms is passed at 180° F.–230° F., say 200° F. to the upper portion of the extractive distillation operation.

It is a particular feature of the process of this invention that it permits ready production and recovery of desired product ether in high purity. The process readily permits product ether to be obtained which is substantially free of methanol and water. These components are undesirable because when the product ether is blended into gasoline formation, (a) methanol will extract water from tank bottoms and (b) water will cause the gasoline to be hazy.

Attempts to remove water from product ether have heretofore not been possible by simple distillation. Removal of methanol from product ether has also been difficult. The solubility of the ether in water also contributes to the problem. In the present process, no water washing of streams containing product ether is necessary, and thus losses of ether are minimized.

DESCRIPTION OF THE SPECIFIC EMBODIMENT

Practice of the process of this invention may be apparent to those skilled in the art from the following wherein, as elsewhere in tis description, all parts are parts by weight unless otherwise specified. It will be apparent that the drawing is schematic and may not show details of the processing technique including eg pumps, vessels, heat exchangers, etc.

In the drawing, the lines are identified as containing the following components:

| A | n-butyl alcohol |
| M | methanol |
| E | methyl t-butyl ether |
| i-B | isobutene |
| B | butanes |

It will be apparent that certain lines bearing a particular label may contain small amounts of other components.

EXAMPLE I

In the drawing which represents practice of a preferred embodiment of the process of this invention, 227 parts of fresh methanol are admitted through line 10 together with 273 parts of recycle methanol admitted through line 11 to form in line 12 a stream containing 500 parts (15.6 moles) of substantially anhydrous methanol. There are also admitted 398 parts of fresh isobutene through line 13 and 102 parts of recycle isobutene through line 14 to form in line 15 a stream containing 500 parts (8.9 moles) of isobutene together with the methanol.

Charge in line 15 is admitted to etherification operation 16 wherein it contacts 87 parts of Amberlyst 15 Sulfonic Acid Resin ion exchange catalyst (Rohm and Haas Inc.) at a WHSV of 11.5 Amberlyst 15 is a cationic, strongly acidic, exchange resin containing a sulfonated polystyrene resin crosslinked with divinyl benzene. Reaction mixture leaves the etherification operation at 200° F. and 300 psig.

Reaction mixture i.e. crude product in line 17 contains 273 parts of methanol, 102 parts of isobutene, 625 parts of methyl t-butyl ether, and 4045 parts of butanes.

This stream is passed to debutanizer 19 which is operated at 100 psig. Overhead recovered at 160° F., in amount of 4147 parts, in line 20 is condensed in condenser 21. Reflux is returned through line 22 and net product, withdrawn through line 23 contains 102 parts of isobutene and 4045 parts of inert hydrocarbons reported as butanes. If the content of isobutene, in line 23, is sufficiently high (ether as recovered due to the low content of butanes in the charge 13, or as a result of purification steps not shown) then the isobutene in line 23 may be passed to line 14 and recycled to charge.

Debutanizer bottoms in line 24, recovered at 220° F., contain 273 parts of methanol and 625 parts of methyl t-butyl ether. This stream is passed to extractive distillation operation 26 to which is also admitted through line 27, 2730 parts of n-butanol at 200° F.

Overhead from extractive distillation which is conducted at 0 psig recovered in line 28 in amount of 625 parts at 131° F. is condensed in condenser 29 and a portion thereof is returned as reflux through line 30. Net product recovered in line 31 is 625 parts of methyl t-butyl ether in purity greater than 99%.

Bottoms from the extractive distillation tower, recovered at 220° F. in line 32 are passed to methanol recovery operation 34. Overhead in line 35 is 273 parts of methanol at 149° F. which is condensed in condenser 36. Reflux is passed through line 37 and net product in amount of 273 parts is withdrawn through line 38. Through line 39, draw off or addition may be made to balance the needs of the system. Preferably all the methanol is recycled through line 11.

Bottoms from the methanol recovery distillation 34 recovered at 243° F. include 2730 parts of n-butanol; and this stream is returned through line 27 to the extractive distillation tower 26. Through line 40 n-butanol may be added to the system or withdrawn.

EXAMPLE II

The process of Example I is carried out using ethanol (in place of methanol) to form ethyl t-butyl ether.

EXAMPLE III

The process of Example I is carried out using i-pentene (in place of i-butylene) to form methyl t-amyl ether.

EXAMPLE IV

The process of Example I is carried out using a mixture of i-butylene and i-pentene (in place of the i-butylene) to form a product mixture of methyl -t-butyl ether and methyl t-amyl ether.

EXAMPLE V

The process of Example I is carried out using a commercial mixture of n-hexanols as the extractive distillation medium.

EXAMPLE VI

The process of Example I is carried out using a commercial mixture of $C_8$ alcohols (marketed as iso-octyl alcohol but which contains a substantial portion of 2-ethylhexanol) as the extractive distillation medium.

EXAMPLE VII

The process of Example I is carried out using trimethylol propane as the extractive distillation medium.

Although this invention has been illustrated by reference to specific embodiments, it will be apparent to those skilled in the art that various changes and modifications may be made which clearly fall within the scope of this invention.

We claim:

1. The method which comprises
   distilling a reaction mixture containing (i) a lower alkanol and (ii) an ether of said lower alkanol and t-butyl alcohol or t-amyl alcohol in an extractive distillation operation in the presence of, as an extractive distillation medium, a $C_2$–$C_8$ aliphatic alcohol having a higher boiling point than said lower alkanol and being substantially miscible therewith thereby forming (iii) extractive distillation overhead containing said ether and (iv) extractive distillation bottoms containing said lower alkanol and extractive distillation medium;
   recovering said extractive distillation overhead containing said ether;
   distilling said extractive distillation bottoms in a distillation operation thereby forming distillation operation overhead containing lower alkanol and distillation operation bottoms containing said extractive distillation medium;
   recovering said distillation operation overhead containing lower alkanol;
   recovering said distillation operation bottoms containing said extractive distillation medium; and
   passing said distillation operation bottoms containing said extractive distillation medium to said extractive distillation operation.

2. The method claimed in claim 1 wherein said extractive distillation medium has a boiling point at least 10° F. higher than the boiling point of said lower alkanol.

3. The method claimed in claim 1 wherein said extractive distillation medium is a monohydroxy alcohol.

4. The method claimed in claim 1 wherein said extractive distillation medium is a $C_4$ to $C_6$ alcohol.

5. The method claimed in claim 1 wherein said extractive distillation medium is a butanol.

6. The method claimed in claim 1 wherein said extractive distillation medium is n-butanol.

7. The method claimed in claim 1 wherein said extractive distillation medium is a hexanol.

8. The method claimed in claim 1 wherein said extractive distillation medium is an octanol.

9. The method claimed in claim 1 wherein said lower alkanol is methanol or ethanol.

10. The method which comprises
    distilling a reaction mixture containing (i) methanol and (ii) an ether of said methanol and t-butyl alcohol or t-amyl alcohol in an extractive distillation operation in the presence of n-butanol thereby forming extractive distillation overhead containing said ether and extractive distillation bottoms containing said methanol and n-butanol;
    recovering said extractive distillation overhead containing said ether;
    distilling said extractive distillation bottoms in a distillation operation thereby forming distillation operation overhead containing methanol and distillation operation bottoms containing n-butanol;
    recovering said distillation operation overhead containing methanol;
    recovering said distillation operation bottoms containing n-butanol; and
    passing said distillation operation bottoms containing n-butanol to said extractive distillation operation.

11. The method which comprises
    distilling a reaction mixture containing (i) a lower alkanol and (ii) an ether of said lower alkanol and t-butyl alcohol or t-amyl alcohol in an extractive distillation operation in the presence of, as an extractive distillation medium, a $C_2$–$C_8$ aliphatic alcohol having a higher boiling point than said lower alkanol and being substantially miscible therewith thereby forming extractive distillation overhead containing said ether and extractive distillation bottoms containing said lower alkanol and extractive distillation medium; and
    recovering said extractive distillation overhead containing said ether.

* * * * *